(12) United States Patent
Chen et al.

(10) Patent No.: US 11,555,871 B2
(45) Date of Patent: Jan. 17, 2023

(54) METHOD OF DETECTING BIOLOGICAL SAMPLE

(71) Applicant: Industrial Technology Research Institute, Hsinchu (TW)

(72) Inventors: Cheng-Tai Chen, Taoyuan (TW); Shih-Ya Chen, Taichung (TW); Yi-Chen Liu, Hsinchu (TW); Ching-Fang Lu, Hsinchu County (TW); Chia-Chen Chang, Hsinchu (TW); Erh-Fang Lee, Taoyuan (TW)

(73) Assignee: Industrial Technology Research Institute, Hsinchu (TW)

( * ) Notice: Subject to any disclaimer, the term of this patent is extended or adjusted under 35 U.S.C. 154(b) by 204 days.

(21) Appl. No.: 17/136,001

(22) Filed: Dec. 29, 2020

(65) Prior Publication Data

US 2021/0199733 A1     Jul. 1, 2021

Related U.S. Application Data

(60) Provisional application No. 62/955,451, filed on Dec. 31, 2019.

(30) Foreign Application Priority Data

Dec. 31, 2019    (TW) .................................. 108148656

(51) Int. Cl.
*G01N 33/98*     (2006.01)
*G01R 33/09*     (2006.01)
(Continued)

(52) U.S. Cl.
CPC ....... *G01R 33/098* (2013.01); *G01N 33/5308* (2013.01); *G01N 33/84* (2013.01)

(58) Field of Classification Search
CPC ......... G01N 33/5308; G01N 33/54333; G01N 33/84; G01R 33/091; G01R 33/093; G01R 33/098; G01R 33/1269
See application file for complete search history.

(56) References Cited

U.S. PATENT DOCUMENTS 8,114,636 B2   2/2012  Agnew et al.
9,738,924 B2   8/2017  Bensimon et al.
(Continued)

FOREIGN PATENT DOCUMENTS

CN    108562575    9/2018
TW    201209169    3/2012

OTHER PUBLICATIONS

Song Li et al., "A Novel SNPs Detection Method Based on Gold Magnetic Nanoparticles Array and Single Base Extension," Theranostics, vol. 2, No. 10, 2012, pp. 967-975.
(Continued)

*Primary Examiner* — Vinh P Nguyen
(74) *Attorney, Agent, or Firm* — JCIPRNET

(57) ABSTRACT

A method of detecting a biological sample includes the following steps. A magnetic sensor chip is provided, wherein the magnetic sensor chip includes a substrate and a magnetic sensing layer located on the substrate. Probes are connected to the magnetic sensor chip. A sample solution containing biological samples labeled with a first marker is provided on the magnetic sensor chip, so that the biological samples labeled with the first marker are hybridized with the probes. Magnetic beads labeled with a second marker are provided on the magnetic sensor chip, so that the magnetic beads labeled with the second marker are bound onto the biological samples labeled with the first marker. A signal sensed by the magnetic sensing layer is detected by a magnetic sensor.

20 Claims, 9 Drawing Sheets

(51) Int. Cl.
*G01N 33/84* (2006.01)
*G01N 33/53* (2006.01)

(56) References Cited

U.S. PATENT DOCUMENTS

| | | | |
|---|---|---|---|
| 10,379,045 | B2 | 8/2019 | Wei et al. |
| 10,605,775 | B2* | 3/2020 | Haratani ............... C12Q 1/68 |
| 11,156,607 | B2* | 10/2021 | Hu .................. G01N 33/54366 |
| 2002/0119470 | A1 | 8/2002 | Nerenberg et al. |
| 2008/0309323 | A1* | 12/2008 | Okano ............... G01N 27/745 |
| | | | 324/204 |
| 2011/0027901 | A1 | 2/2011 | Gaster et al. |
| 2015/0299769 | A1* | 10/2015 | Grosshauser ........ C12N 15/101 |
| | | | 435/6.12 |
| 2018/0313789 | A1 | 11/2018 | Rizzi et al. |
| 2019/0218600 | A1 | 7/2019 | De Regt et al. |

OTHER PUBLICATIONS

M.M.Miller et al., "A DNA array sensor utilizing magnetic microbeads and magnetoelectronic detection," Journal of Magnetism and Magnetic Materials, vol. 225, Issues 1-2, 2001, pp. 138-144.

Monty Liong et al., "Magnetic barcode assay for genetic detection of pathogens," nature communications, vol. 4, Article No. 1752, Apr. 23, 2013, pp. 1-9.

Giovanni Rizzi et al., "Denaturation strategies for detection of double stranded PCR products on GMR magnetic biosensor array," Biosensors and Bioelectronics, vol. 93, Jul. 15, 2017, pp. 155-160.

Sharmili Roy et al., "Paper-based rapid detection of pork and chicken using LAMP-magnetic bead aggregates," Analytical Methods, vol. 8, Issue 11, Feb. 2016, pp. 2391-2399.

H. Cumhur Tekin et al., "Attomolar protein detection using a magnetic bead surface coverage assay," Lab on a Chip, vol. 13, Issue 6, Jan. 2013, pp. 1053-1059.

Kang-Yi Lien et al., "Rapid detection of influenza A virus infection utilizing an immunomagnetic bead-based microfluidic system," Biosens Bioelectron., vol. 26, No. 9, May 15, 2011, pp. 3900-3907.

Jwa-Min Nam et al., "Nanoparticle-Based Bio-Bar Codes for the Ultrasensitive Detection of Proteins," Science, vol. 301, Issue 5641, Sep. 26, 2003, pp. 1884-1886.

Savka I. Stoeva et al., "Multiplexed DNA Detection with Biobarcoded Nanoparticle Probes," Angewandte Chemie International Edition, vol. 45, Issue 20, May 5, 2006, pp. 3303-3306.

\* cited by examiner

METHOD OF DETECTING BIOLOGICAL SAMPLE

CROSS-REFERENCE TO RELATED APPLICATION

This application claims the priority benefits of U.S. provisional application Ser. No. 62/955,451, filed on Dec. 31, 2019 and Taiwan application serial no. 108148656, filed on Dec. 31, 2019. The entirety of each of the above-mentioned patent applications is hereby incorporated by reference herein and made a part of this specification.

TECHNICAL FIELD

The technical field relates to a detection method, and particularly to a method of detecting a biological sample.

BACKGROUND

At present, biological samples are generally detected using traditional optical detection techniques. However, traditional optical detection techniques are not effective in optically identifying low-concentration biological samples, and are susceptible to background matrix interference during spectral identification, thus resulting in a reduced detection sensitivity. Therefore, the development of a detection technique and method not limited by optical identification is currently an important topic in this field.

SUMMARY

The disclosure provides a method of detecting a biological sample including the following steps. A magnetic sensor chip is provided, wherein the magnetic sensor chip includes a substrate and a magnetic sensing layer located on the substrate. A plurality of probes are connected to the magnetic sensor chip. A sample solution including a plurality of biological samples labeled with a first marker is provided on the magnetic sensor chip, so that the biological samples labeled with the first marker are hybridized with the probes. A plurality of magnetic beads labeled with a second marker are provided on the magnetic sensor chip, so that the magnetic beads labeled with the second marker are bound onto the biological samples labeled with the first marker. A signal sensed by the magnetic sensing layer is detected by a magnetic sensor.

Based on the above, in the method of detecting the biological sample provided by the disclosure, when detection is performed using the magnetic sensor in the magnetic sensor chip, since there is almost no magnetic substance in the biological samples, interference by the matrix does not occur.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure. It will be apparent, however, that one or more embodiments may be practiced without these specific details.

DETAILED DESCRIPTION OF DISCLOSED EMBODIMENTS

Figure 1:
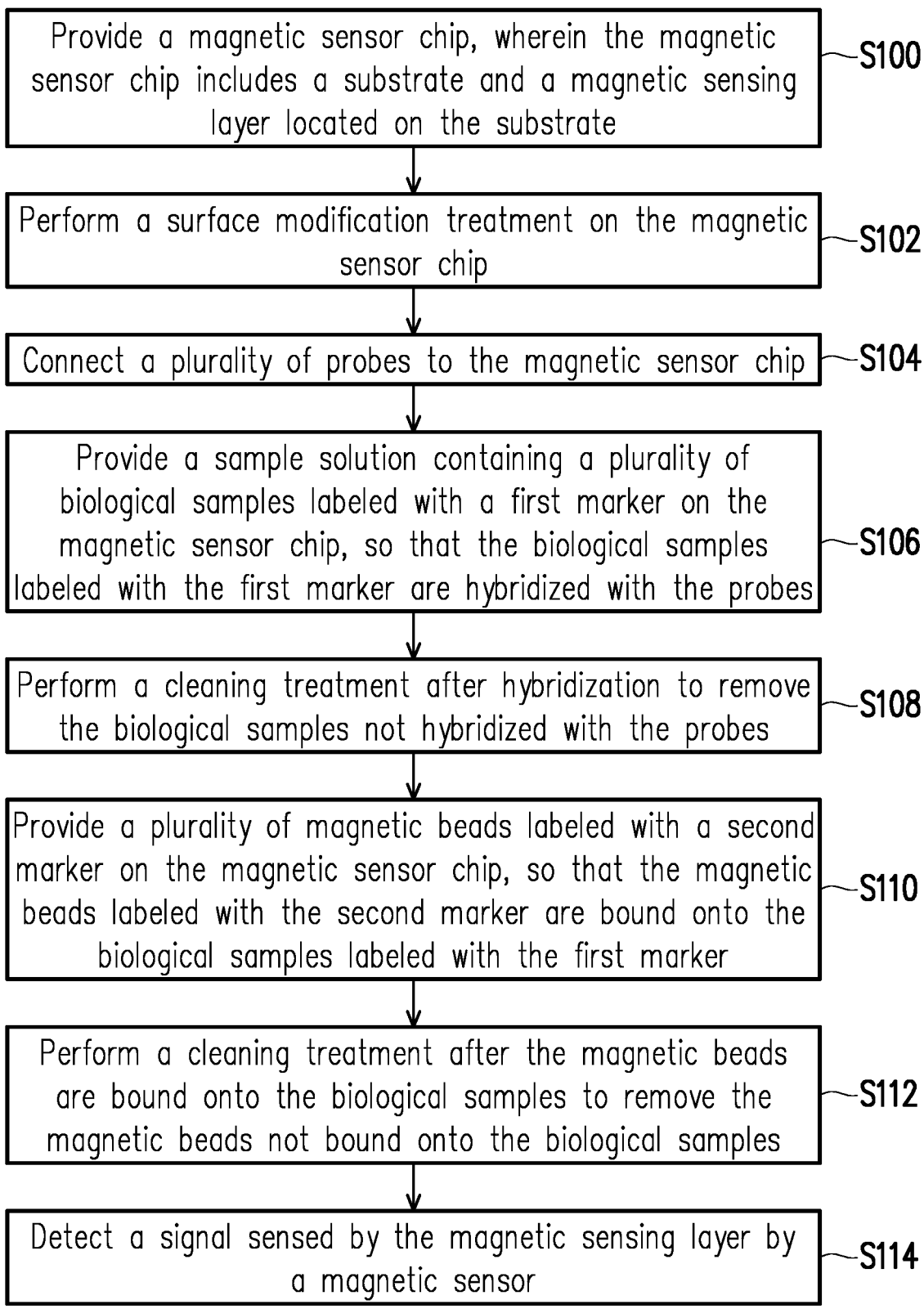
FIG. 1 is a flowchart of a method of detecting a biological sample of an embodiment of the disclosure.
Figure 3:
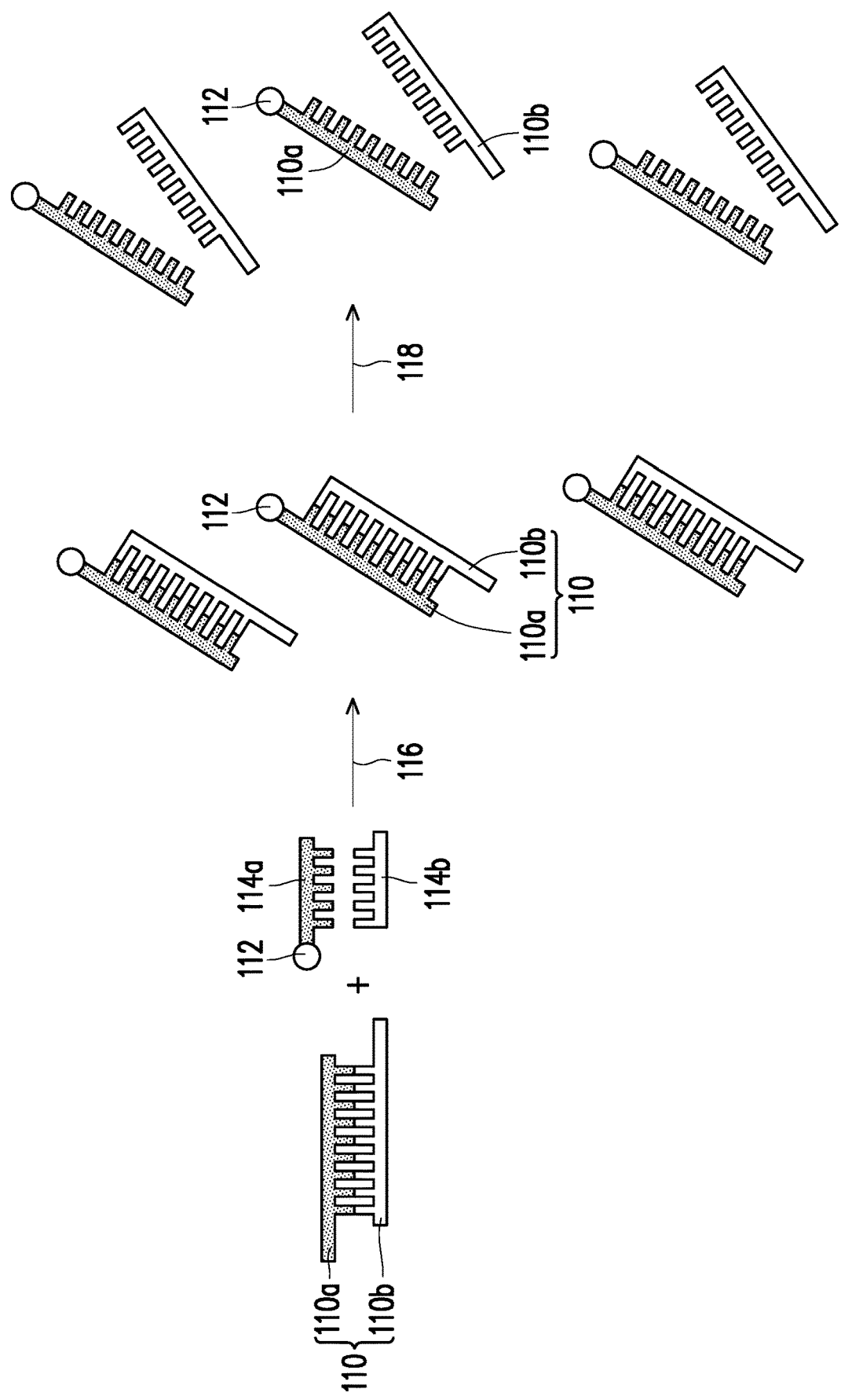
FIG. 3 is a diagram of a method of preparing a biological sample of an embodiment of the disclosure.
Figure 4:
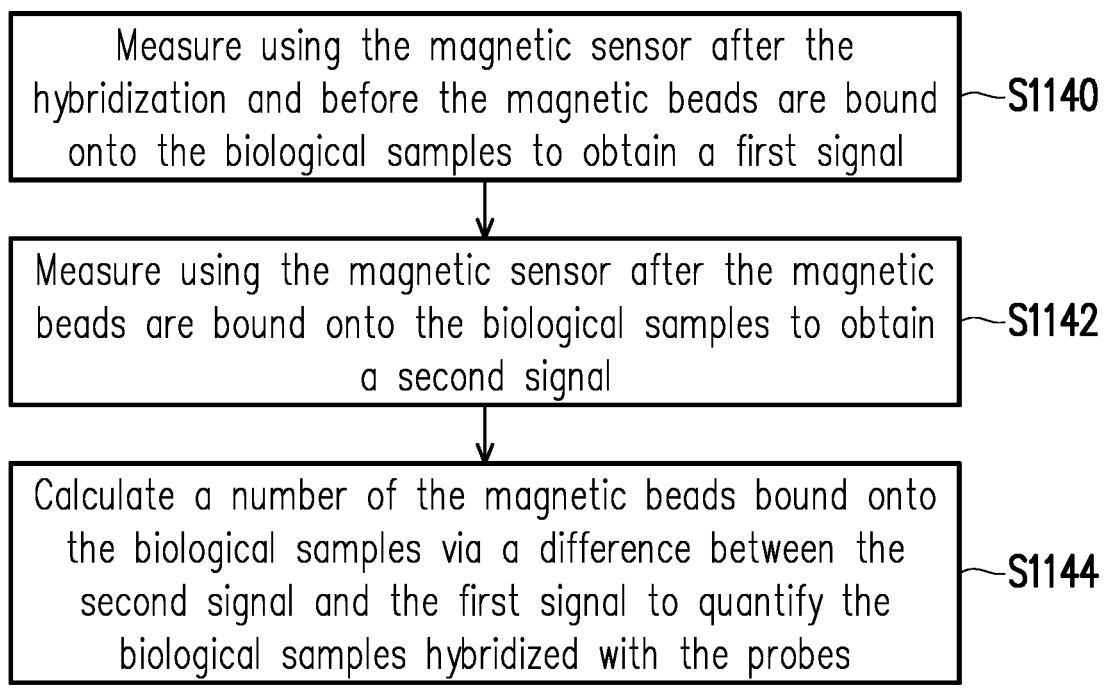
FIG. 4 is a flowchart of quantitative analysis of an embodiment of the disclosure.

FIG. 1 is a flowchart of a method of detecting a biological sample of an embodiment of the disclosure. FIG. 2A to FIG. 2F are diagrams of a process of detecting a biological sample of an embodiment of the disclosure. FIG. 3 is a diagram of a method of preparing a biological sample of an embodiment of the disclosure. FIG. 4 is a flowchart of quantitative analysis of an embodiment of the disclosure.

Figure 2A:
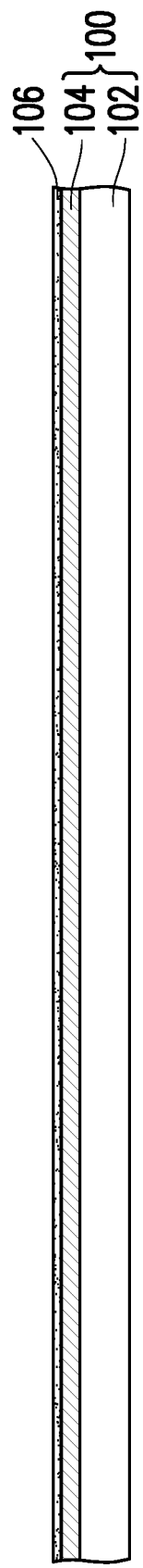
FIG. 2A to FIG. 2F are diagrams of a process of detecting a biological sample of an embodiment of the disclosure.

Referring to FIG. 1 and FIG. 2A, step S100 is performed to provide a magnetic sensor chip 100. The magnetic sensor chip 100 refers to a chip containing a magnetic sensor. In the present embodiment, the magnetic sensor chip 100 includes a substrate 102 and a magnetic sensing layer 104 located on the substrate 102. The substrate 102 is, for example, a semiconductor substrate, such as a silicon substrate. The magnetic sensing layer 104 may be a magnetic tunnel junction (MTJ) structure. For example, the magnetic tunnel junction structure may be a sandwich structure containing two (upper and lower) ferromagnetic metal layers (such as NiFe or CoFe) and an insulating layer (such as aluminum oxide or magnesium oxide) in between. The magnetic sensing layer 104 may be manufactured by a semiconductor process. In some embodiments, the magnetic sensor chip 100 may be a microfluidic chip, but the disclosure is not limited thereto.

In addition, step S102 may be performed to perform a surface modification treatment on the magnetic sensor chip 100 to facilitate connecting the probes to the magnetic sensor chip 100 in a subsequent manufacturing process. The surface modification treatment is, for example, to form a silicon dioxide dielectric layer 106 on the magnetic sensor chip 100, but the disclosure is not limited thereto. For example, the silicon dioxide dielectric layer 106 may be formed on the magnetic sensing layer 104. In other embodiments, the surface modification treatment may be to form a dielectric layer of other suitable materials on the magnetic sensor chip 100.

Figure 2B:
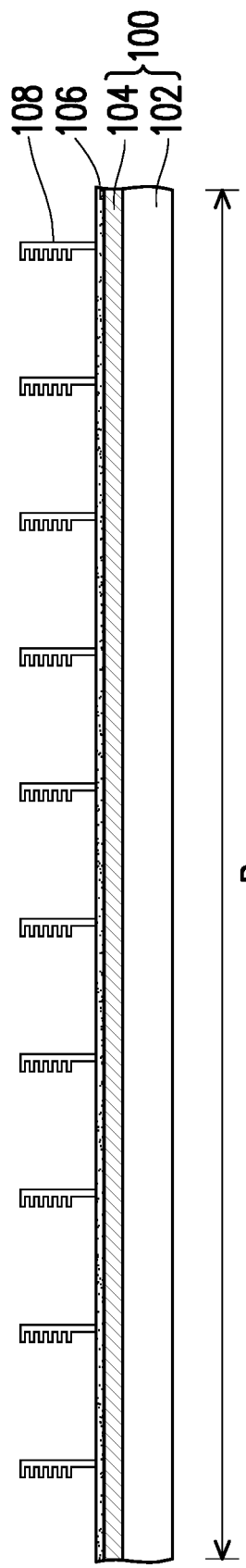

Referring to FIG. 1 and FIG. 2B, step S104 is performed to connect a plurality of probes 108 on the magnetic sensor chip 100. For example, the probes 108 may be connected to the silicon dioxide dielectric layer 106. In addition, the probes 108 may be located in a sensing region R of the magnetic sensor chip 100. The sensing region R of the magnetic sensor chip 100 may be a well or a flow channel in the magnetic sensor chip 100. In the present embodiment, the probes 108 are nucleic acid probes as an example, but the disclosure is not limited thereto. In addition, the length of the nucleic acid probes is, for example, 20 monomer units to 40 monomer units, for example, about 20 monomer units to 25 monomer units, about 25 monomer units to 30 monomer units, about 30 monomer units to 35 monomer units, or about 35 monomer units to 40 monomer units, but is not limited thereto. In an embodiment, the length of the nucleic acid probes may be 20 monomer units to 30 monomer units. The method of connecting the probes 108 to the magnetic sensor chip 100 is, for example, a chemical cross-linking method.

Figure 2C:
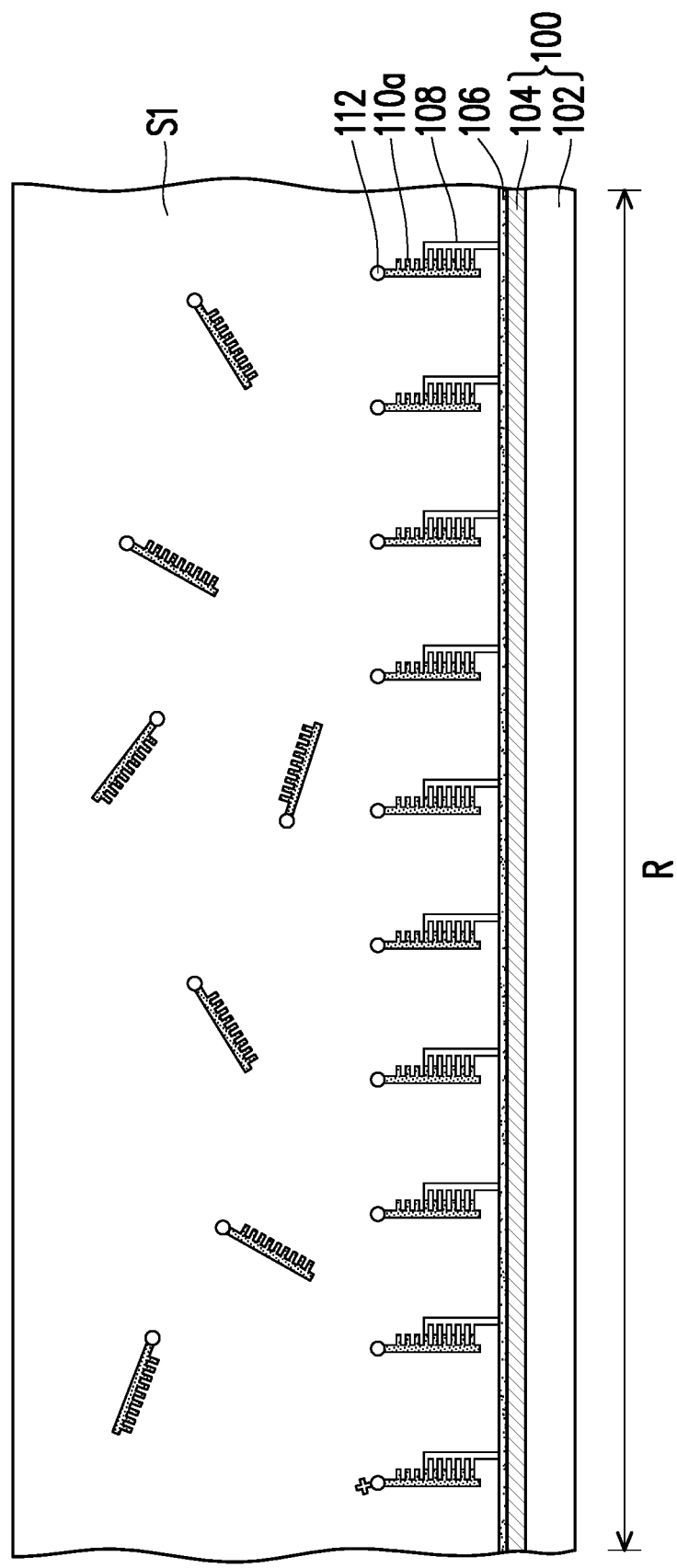

Referring to FIG. 1 and FIG. 2C, step S106 is performed to provide a sample solution S1 including a plurality of biological samples labeled with a first marker 112 on the magnetic sensor chip 100, so that the biological samples labeled with the first marker 112 are hybridized with the probes 108. The source of the biological samples may be a biological specimen to be tested. The biological specimen to be tested is, for example, urine, saliva, serum, or plasma. In a case where the source of the biological samples is the biological specimen to be tested, the biological specimen to be tested may be pre-treated by an extraction treatment or a purification treatment, for example. The temperature range of the hybridization is, for example, 45° C. to 65° C., but the disclosure is not limited thereto. For example, the temperature range of the hybridization may be about 45° C. to 50° C., about 50° C. to 55° C., about 55° C. to 60° C., or about 60° C. to 65° C., etc., but is not limited thereto. In an embodiment, the temperature range of the hybridization may be about 55° C. to 62° C., thereby shortening the reaction time. In some embodiments, the temperature range of the hybridization may be about 50° C., about 55° C., or about 60° C.

In the present embodiment, the biological samples are a single-stranded nucleic acid 110*a* to be tested as an example, but the disclosure is not limited thereto. The length of the single-stranded nucleic acid 110*a* to be tested is, for example, 80 monomer units to 120 monomer units, for example, about 80 monomer units to 90 monomer units, about 90 monomer units to 100 monomer units, about 100 monomer units to 110 monomer units, or about 110 monomer units to 120 monomer units, but is not limited thereto. In an embodiment, the length of the single-stranded nucleic acid 110*a* to be tested may be 90 monomer units to 110 monomer units. The first marker 112 may be biotin, but the disclosure is not limited thereto.

Referring to FIG. 3, when the biological samples are the single-stranded nucleic acid 110*a* to be tested, the method of preparing the biological samples labeled with the first marker 112 may include the following steps, but the disclosure is not limited thereto. A double-stranded nucleic acid 110 to be tested is provided. For example, the double-stranded nucleic acid 110 to be tested may be obtained by pre-treating a biological specimen to be tested. The double-stranded nucleic acid 110 to be tested may include the single-stranded nucleic acid 110*a* to be tested and a single-stranded nucleic acid 110*b*. Next, an amplification treatment 116 is performed on the double-stranded nucleic acid 110 to be tested using a primer 114*a* labeled with the first marker 112 to obtain a plurality of double-stranded nucleic acids 110 to be tested labeled with the first marker 112. The amplification treatment of the double-stranded nucleic acid to be tested is, for example, a polymerase chain reaction (PCR). In the amplification treatment 116, a pair of the primer 114*a* and a primer 114*b* may be used for amplification. Then, a denaturation treatment 118 is performed on the double-stranded nucleic acids 110 to be tested labeled with the first marker 112 to obtain the sample solution S1 of the single-stranded nucleic acid 110*a* to be tested labeled with the first marker 112 (FIG. 2C). In addition, the sample solution S1 may include the single-stranded nucleic acid 110*b* (not shown in FIG. 2C) in addition to the single-stranded nucleic acid 110*a* to be tested. That is, the double-stranded nucleic acids 110 to be tested may form the single-stranded nucleic acid 110*a* to be tested and the single-stranded nucleic acid 110*b* labeled with the first marker 112 via the denaturation treatment 118. The denaturation treatment 118 is, for example, a pyrolysis treatment.

Figure 2D:
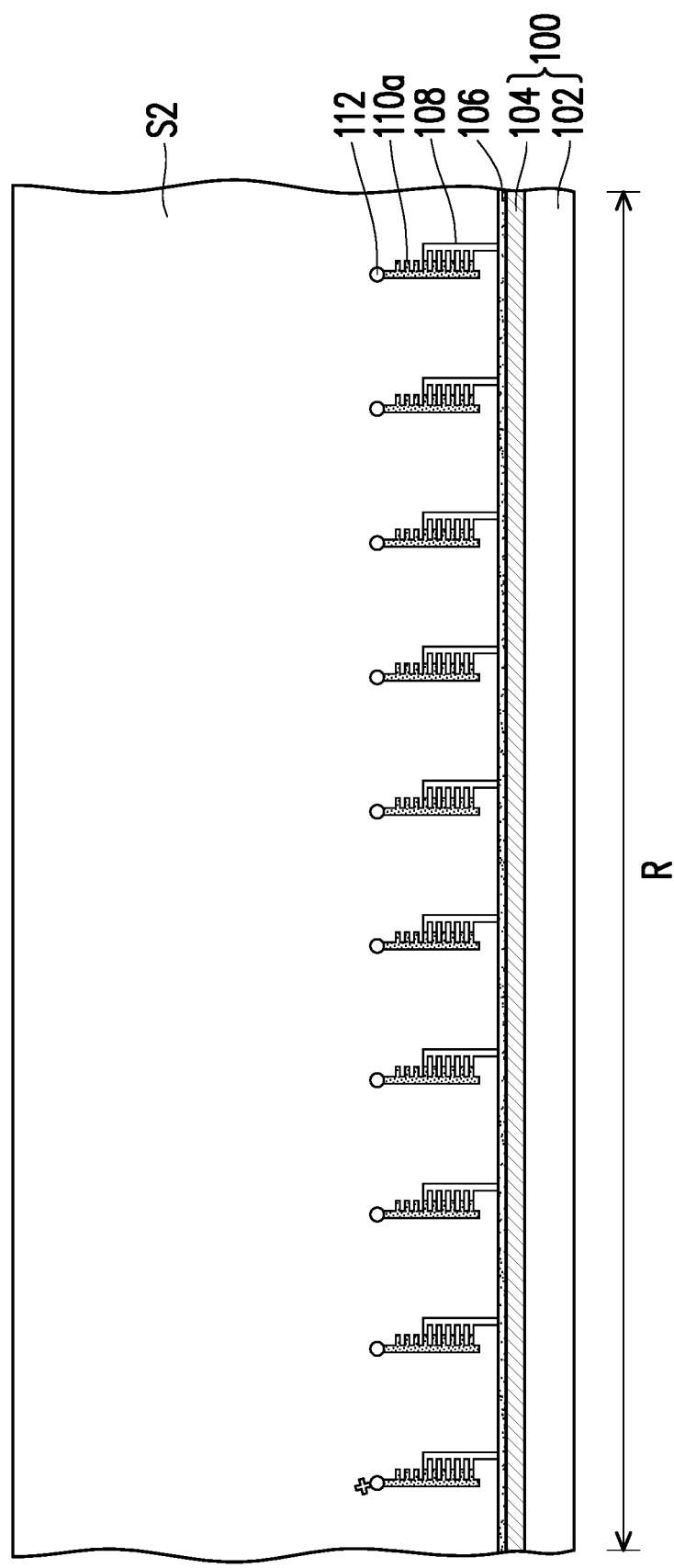

Referring to FIG. 1 and FIG. 2D, step S108 may be performed to perform a cleaning treatment after the hybridization to remove the biological samples not hybridized with the probes 108 (e.g., the single-stranded nucleic acid 110*a* to be tested). For example, the cleaning treatment may be performed using a buffer S2. The buffer S2 is, for example, a Tris (product name) buffer, but the disclosure is not limited thereto. The Tris buffer may contain tris(hydroxymethyl) aminomethane (Tris), sodium chloride (NaCl), and Tween 20 (product name, manufactured by Sigma Aldrich). In an embodiment, the pH of the Tris buffer may be 7.6, and may include Tris at a concentration of 0.05 M, NaCl at a concentration of 0.15 M, and Tween 20 at 0.02% (v/v). In other embodiments, the cleaning treatment of step S108 may be omitted.

Figure 2E:
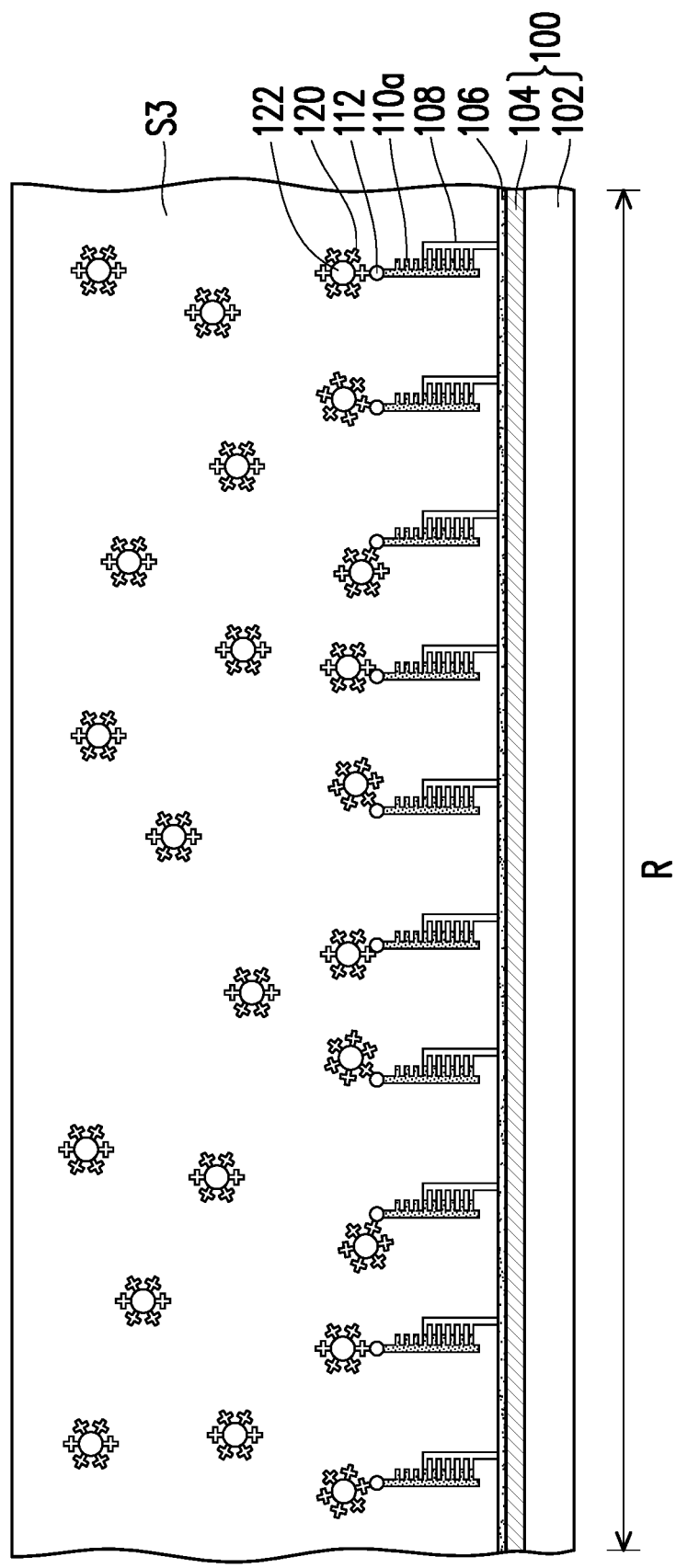

Referring to FIG. 1 and FIG. 2E, step S110 is performed to provide a plurality of magnetic beads 122 labeled with a second marker 120 on the magnetic sensor chip 100 so that the magnetic beads 122 labeled with the second marker 120 are bound onto the biological samples (for example, the single-stranded nucleic acid 110*a* to be tested) labeled with the first marker 112. For example, the magnetic beads 122 labeled with the second marker 120 may be prepared into a magnetic bead solution S3 in advance, and then the magnetic bead solution S3 is provided on the magnetic sensor chip 100. In addition, the magnetic beads 122 may be bound onto the biological samples (e.g., the single-stranded nucleic acid 110*a* to be tested) by the affinity between the second marker 120 and the first marker 112. In the present embodiment, when the first marker 112 is biotin, the second marker 120 may be Streptavidin, but the disclosure is not limited thereto. The method of preparing the magnetic beads 122 labeled with the second marker 120 is, for example, a chemical reduction method. The magnetic beads 122 may be hollow magnetic beads or solid magnetic beads. The particle size of the magnetic beads 122 is, for example, 0.2 μm to 2 μm. The material of the magnetic beads 122 is, for example, iron (II,III) oxide ($Fe_3O_4$), nickel iron oxide ($NiFe_2O_4$), or cobalt iron oxide ($CoFe_2O_4$).

Figure 2F:
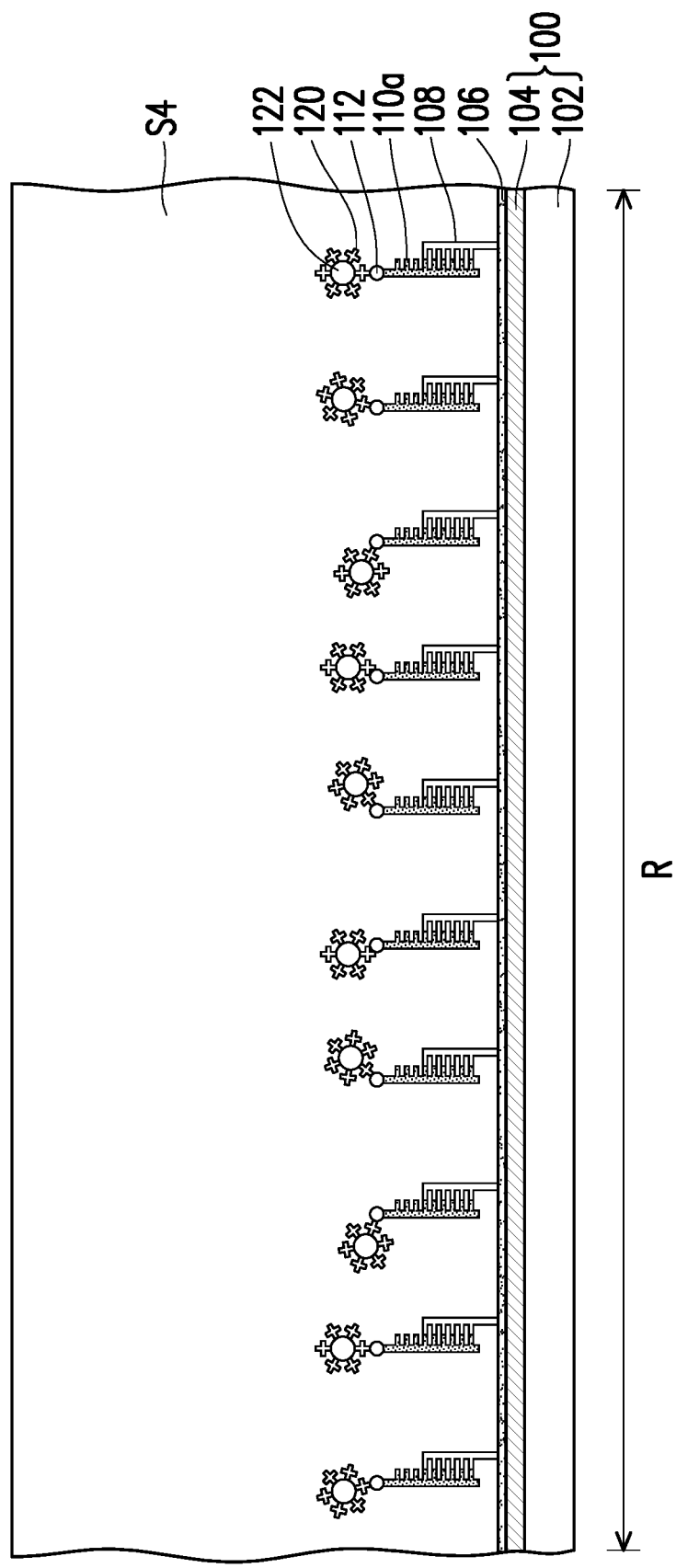

Referring to FIG. 1 and FIG. 2F, step S112 may be performed to perform a cleaning treatment after the magnetic beads 122 are bound onto the biological samples (e.g., the single-stranded nucleic acid 110*a* to be tested) to remove the magnetic beads 122 not bound onto the biological samples (e.g., the single-stranded nucleic acid 110*a* to be tested). For example, the cleaning treatment may be performed using a buffer S4. The buffer S4 is, for example, a Tris buffer, but the disclosure is not limited thereto. The Tris buffer may contain Tris, NaCl, and Tween 20 (product name, manufactured by Sigma Aldrich). In an embodiment, the pH of the Tris buffer may be 7.6, and may include Tris at a concentration of 0.05 M, NaCl at a concentration of 0.15 M, and Tween 20 at 0.02% (v/v). In other embodiments, the cleaning treatment of step S112 may be omitted.

Referring to FIG. 1, FIG. 2F, and FIG. 4, step S114 is performed to detect a signal sensed by the magnetic sensing layer 104 by a magnetic sensor. The magnetic sensor is, for example, a tunnel magnetoresistance (TMR) sensor or a giant magnetoresistance (GMR) sensor. The detection performed by the magnetic sensor may further include quantitative analysis or qualitative analysis. That is, the method of detecting the biological sample of the present embodiment may be used for qualitative detection and quantitative detection of various diseases. In the present embodiment, the detection performed by the magnetic sensor is explained by taking quantitative analysis as an example.

For example, the quantitative analysis may include the following steps. First, step S1140 is performed. After the hybridization and before the magnetic beads 122 are bound onto the biological samples (e.g., the single-stranded nucleic acid 110a to be tested), measurement is performed using a magnetic sensor to obtain a first signal. Next, step S1142 is performed. After the magnetic beads 122 are bound onto the biological samples (e.g., the single-stranded nucleic acid 110a to be tested), measurement is performed using the magnetic sensor to obtain a second signal. Next, step S1144 is performed to calculate the number of the magnetic beads 122 bound onto the biological samples (e.g., the single-stranded nucleic acid 110a to be tested) by the difference between the second signal and the first signal to quantify the biological samples (for example, the single-stranded nucleic acid 110a to be tested) hybridized with the probes 108. The first signal and the second signal may be measured at room temperature to reduce the influence of temperature variation on the signal. The first signal and the second signal are, for example, voltage signals. When the first signal and the second signal are voltage signals, the voltage value of the second signal when the magnetic beads 122 are bound onto the biological samples (e.g., the single-stranded nucleic acid 110a to be tested) may be higher than the voltage value of the first signal when the magnetic beads 122 are not bound onto the biological samples (e.g., the single-stranded nucleic acid 110a to be tested). The measurement mode of the magnetic sensor may be a real-time measurement mode. For example, the real-time measurement mode may continuously perform measurement from step S106 to step S114.

In other embodiments, in the case of qualitative analysis using a magnetic sensor, as long as the second signal is significantly different from the first signal, it may be determined that the biological samples (e.g., the single-stranded nucleic acid 110a to be tested) are hybridized with the probes 108.

Based on the above embodiments, it may be known that in the method of detecting the biological sample, when detection is performed using the magnetic sensor in the magnetic sensor chip 100, since there is almost no magnetic substance in the biological samples, interference by the matrix does not occur. In this way, when the biological samples are detected using the magnetic sensor in the magnetic sensor chip 100, better detection sensitivity may be achieved.

Experimental Example

Figure 5:
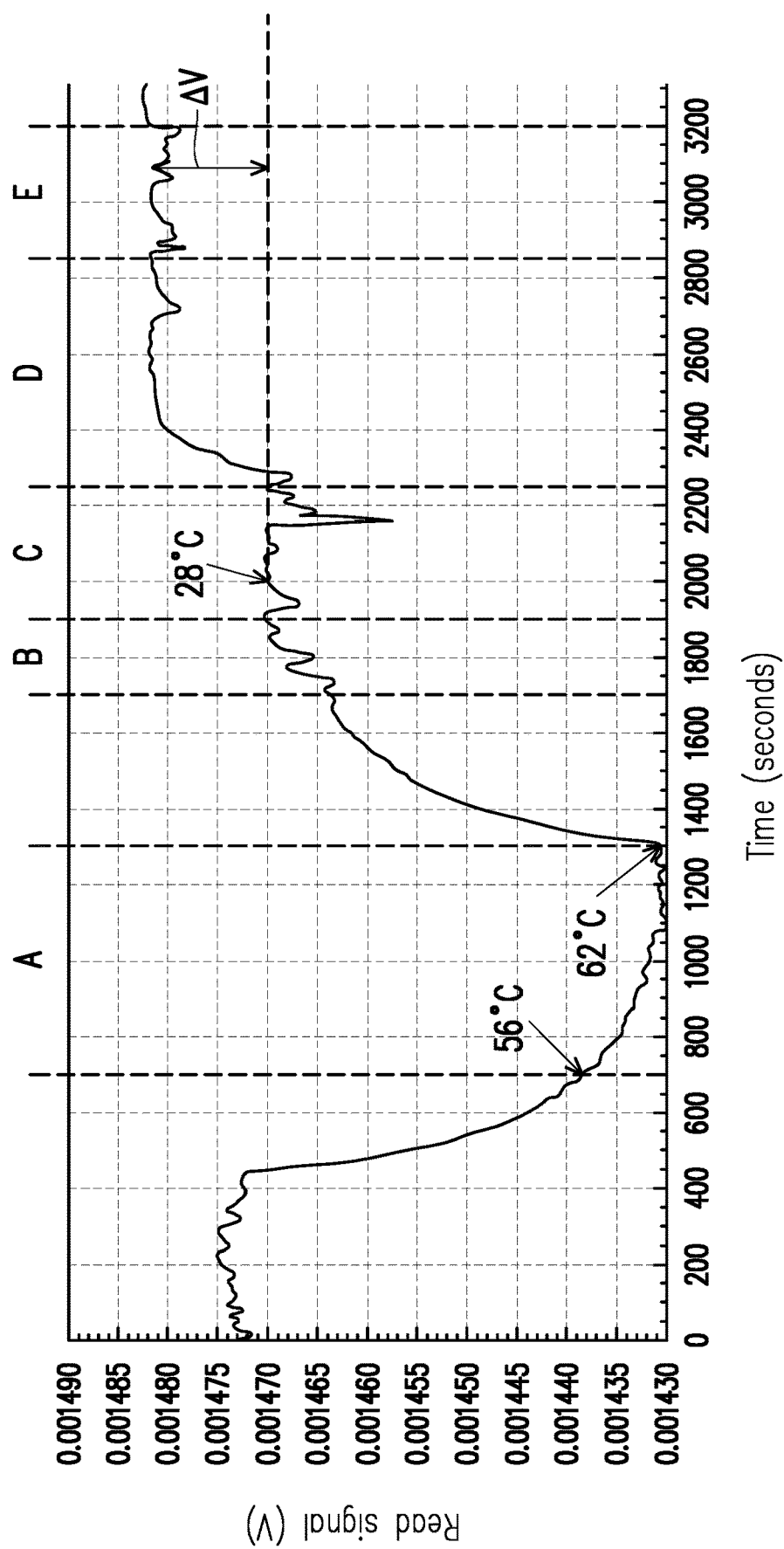
FIG. 5 is a diagram showing the relationship between read signal and time of an experimental example of the disclosure.

FIG. 5 is a diagram showing the relationship between read signal and time of an experimental example of the disclosure.

Referring to FIG. 5, after the single-stranded nucleic acid labeled with biotin (biological samples) is detected by the method of detecting biological samples of the above embodiments, the obtained detection results are described as follows.

At about 400 seconds, a single-stranded nucleic acid to be tested labeled with biotin was added to a sensing region of the magnetic sensor chip to be hybridized with the nucleic acid probes in the sensing region. At about 700 seconds to about 1300 seconds, the temperature was increased to 56° C. to 62° C., and hybridization was performed for 10 minutes (section A). By increasing the temperature to 56° C. to 62° C., the hybridization was accelerated. In section A, the signal was decreased due to the increase in temperature.

At about 1300 seconds, the temperature began to drop to room temperature, at which time the signal was increased due to the decrease in temperature.

At about 1700 seconds, the sensing region was cleaned with a Tris buffer, and the single-stranded nucleic acid to be tested not hybridized with the nucleic acid probes was washed away from the sensing region (section B). The pH of the Tris buffer was 7.6, and included Tris at a concentration of 0.05 M, NaCl at a concentration of 0.15 M, and Tween 20 at 0.02% (v/v).

At about 2000 seconds, the temperature was returned to room temperature (for example, 28° C.), and a signal was measured using a tunnel magnetoresistance (TMR) sensor of the magnetic sensor chip, and the signal at this time was used as the initial signal of the measurement (section C).

At about 2200 seconds, magnetic beads labeled with Streptavidin were added and reacted for 10 minutes at room temperature so that the magnetic beads labeled with Streptavidin were bound onto the single-stranded nucleic acid labeled with biotin, and a magnetic signal reaction was generated by the magnetic beads (section D).

At about 2800 seconds, the sensing region was cleaned with a Tris buffer, and the magnetic beads not bound onto the single-stranded nucleic acid to be tested were washed away from the sensing region. The pH of the Tris buffer was 7.6, and included Tris at a concentration of 0.05 M, NaCl at a concentration of 0.15 M, and Tween 20 at 0.02% (v/v). In addition, the signal measured by the tunnel magnetoresistance (TMR) sensor in this section (section E) was subtracted with the initial signal (section C) before the magnetic beads were added to obtain the voltage difference $\Delta V$ (about 12.5 $\mu V$). With this voltage difference, the number of single-stranded nucleic acid to be tested hybridized with the nucleic acid probes in the sensing region was calculated.

Based on the above, in the method of detecting biological samples of the above embodiments, when detection is performed using the magnetic sensor in the magnetic sensor chip, since there is almost no magnetic substance in the biological samples, interference by the matrix does not occur. In this way, when the biological samples are detected using the magnetic sensor in the magnetic sensor chip, better detection sensitivity may be achieved.

It will be apparent to those skilled in the art that various modifications and variations may be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A method of detecting a biological sample, comprising:
providing a magnetic sensor chip, wherein the magnetic sensor chip comprises a substrate and a magnetic sensing layer located on the substrate;
connecting a plurality of probes to the magnetic sensor chip;
providing a sample solution containing a plurality of biological samples labeled with a first marker on the magnetic sensor chip, so that the plurality of biological samples labeled with the first marker are hybridized with the plurality of probes;
providing a plurality of magnetic beads labeled with a second marker on the magnetic sensor chip, so that the plurality of magnetic beads labeled with the second marker are bound onto the plurality of biological samples labeled with the first marker; and detecting a signal sensed by the magnetic sensing layer by a magnetic sensor.

2. The method of detecting the biological sample of claim 1, wherein the magnetic sensor comprises a tunnel magnetoresistance (TMR) sensor or a giant magnetoresistance (GMR) sensor.

3. The method of detecting the biological sample of claim 1, wherein the plurality of probes comprise nucleic acid probes.

4. The method of detecting the biological sample of claim 3, wherein a length of the nucleic acid probes is 20 monomer units (mer) to 40 monomer units.

5. The method of detecting the biological sample of claim 1, wherein the plurality of probes are located in a sensing region of the magnetic sensor chip.

6. The method of detecting the biological sample of claim 1, wherein the plurality of biological samples comprise a single-stranded nucleic acid to be tested.

7. The method of detecting the biological sample of claim 6, wherein a length of the single-stranded nucleic acid to be tested is 80 monomer units to 120 monomer units.

8. The method of detecting the biological sample of claim 6, wherein a method of preparing the plurality of biological samples labeled with the first marker comprises:

providing a double-stranded nucleic acid to be tested;

performing an amplification treatment on the double-stranded nucleic acid to be tested using a primer labeled with the first marker to obtain a plurality of the double-stranded nucleic acid to be tested labeled with the first marker; and performing a denaturation processing on the plurality of double-stranded nucleic acids to be tested labeled with the first marker to obtain the sample solution of the plurality of single-stranded nucleic acids to be tested labeled with the first marker.

9. The method of detecting the biological sample of claim 8, wherein the amplification treatment of the double-stranded nucleic acid to be tested comprises performing a polymerase chain reaction (PCR), and the denaturation treatment comprises a thermal decomposition treatment.

10. The method of detecting the biological sample of claim 1, wherein a source of the biological samples comprises a biological specimen to be tested, and the biological specimen to be tested comprises urine, saliva, serum, or plasma.

11. The method of detecting the biological sample of claim 1, wherein the first marker comprises biotin, and the second marker comprises Streptavidin.

12. The method of detecting the biological sample of claim 1, wherein a particle size of the magnetic beads is 0.2 μm to 2 μm.

13. The method of detecting the biological sample of claim 1, wherein a material of the magnetic beads comprises iron (II,III) oxide ($Fe_3O_4$), nickel iron oxide ($NiFe_2O_4$), or cobalt iron oxide ($CoFe_2O_4$).

14. The method of detecting the biological sample of claim 1, wherein the detection performed by the magnetic sensor further comprises a quantitative analysis, and the quantitative analysis comprises:

measuring using the magnetic sensor after the hybridization and before the plurality of magnetic beads are bound onto the plurality of biological samples to obtain a first signal;

measuring using the magnetic sensor after the plurality of magnetic beads are bound onto the plurality of biological samples to obtain a second signal; and calculating a number of the plurality of magnetic beads bound onto the plurality of biological samples by a difference between the second signal and the first signal to quantify the plurality of biological samples hybridized with the plurality of probes.

15. The method of detecting the biological sample of claim 14, wherein the first signal and the second signal comprise voltage signals, and a voltage value of the second signal is higher than a voltage value of the first signal.

16. The method of detecting the biological sample of claim 14, wherein the first signal and the second signal are measured at room temperature.

17. The method of detecting the biological sample of claim 1, further comprising:

performing a surface modification treatment on the magnetic sensor chip before the plurality of probes are connected to the magnetic sensor chip.

18. The method of detecting the biological sample of claim 17, wherein the surface modification treatment comprises forming a silicon dioxide dielectric layer on the magnetic sensor chip.

19. The method of detecting the biological sample of claim 1, further comprising:

performing a cleaning treatment after the hybridization to remove the biological samples not hybridized with the plurality of probes.

20. The method of detecting the biological sample of claim 1, further comprising:

performing a cleaning treatment after the plurality of magnetic beads are bound onto the plurality of biological samples to remove the magnetic beads not bound onto the plurality of biological samples.

* * * * *